US00PP23858P3

(12) United States Plant Patent
Biel et al.

(10) Patent No.: US PP23,858 P3
(45) Date of Patent: Aug. 27, 2013

(54) ***CHLAMYDOMONAS REINHARDTII* ALGA VARIETY NAMED 'DG8-108'**

(50) Latin Name: *Chlamydomonas reinhardtii*
Varietal Denomination: DG8-108

(76) Inventors: Karl Y. Biel, Tucson, AZ (US); Vladimir G. Ladygin, Pushchino (RU); Calvin M. Nii, Boulder, CO (US)

( * ) Notice: Subject to any disclaimer, the term of this patent is extended or adjusted under 35 U.S.C. 154(b) by 35 days.

(21) Appl. No.: 13/066,575

(22) Filed: Apr. 18, 2011

(65) Prior Publication Data

US 2012/0264195 P1 Oct. 18, 2012

(51) Int. Cl.
*A01H 5/00* (2006.01)

(52) U.S. Cl.
USPC ..... Plt./395

(58) Field of Classification Search
USPC ..... Plt./395
See application file for complete search history.

*Primary Examiner* — Susan McCormick Ewoldt

(57) ABSTRACT

A novel variety of the unicellular green algae *Chlamydomonas reinhardtii*, named 'DG8-108', was created by exposing wild-type *C. reinhardtii* to γ-radiation exposure. This new and distinct alga variety demonstrates nearly double the biomass and photosynthetic productivity of wild-type *C. reinhardtii* under both optimal and stress conditions.

5 Drawing Sheets

I. BACKGROUND OF THE INVENTION

This application describes a new and distinct variety of alga named *Chlamydomonas reinhardtii*, 'DG8-108', that can accumulate 2.5 times more biomass on mineral medium and under photosynthesis, compared to wild-type *C. reinhardtii*, under optimal and stressful environmental conditions. 'DG8-108' was developed for use in plant physiological research and in the commercial production of bioproducts.

*Chlamydomonas* is a genus of unicellular green algae (phylum Chlorophyta; class Chlorophyceae). These algae are found in soil, fresh water, oceans, and even in snow on mountaintops. Algae in this genus have a cell wall, a chloroplast, an "eyespot" that perceives light, and two anterior flagella with which they can swim using a breast-stroke type motion. More than 500 different species of *Chlamydomonas* have been described, but most scientists work with only a few species.

The most widely used laboratory species is *Chlamydomonas reinhardtii* (Dang). The wild-type of this species (137-C) was isolated from soil by Dr. Smith in 1948 in USA (see in rf. Levine 1960). Cells of this wild-type variety are haploid, and can grow on a simple liquid or solid medium of inorganic salts, using photosynthesis to provide energy. Cells can also grow in total darkness when acetate is provided as an alternative carbon source. When deprived of nitrogen, haploid cells of opposite mating types can fuse to form a diploid zygospore which forms a hard outer wall that protects it from adverse environmental conditions. When conditions improve (e.g. when nitrogen is restored to the culture medium), the diploid zygote undergoes meiosis and releases four haploid cells that resume the vegetative life cycle.

We used *C. reinhardtii* variety 137C, which was originally sent to us by Dr. R. P. Levine in 1965, to create the *C. reinhardtii* variety 'DG8-108' described herein to facilitate investigation of general plant physiological phenomena. This novel variety has been created, isolated, cultivated and maintained as a pure algal culture in laboratories in Puschino, Russian Federation.

Figure 1:
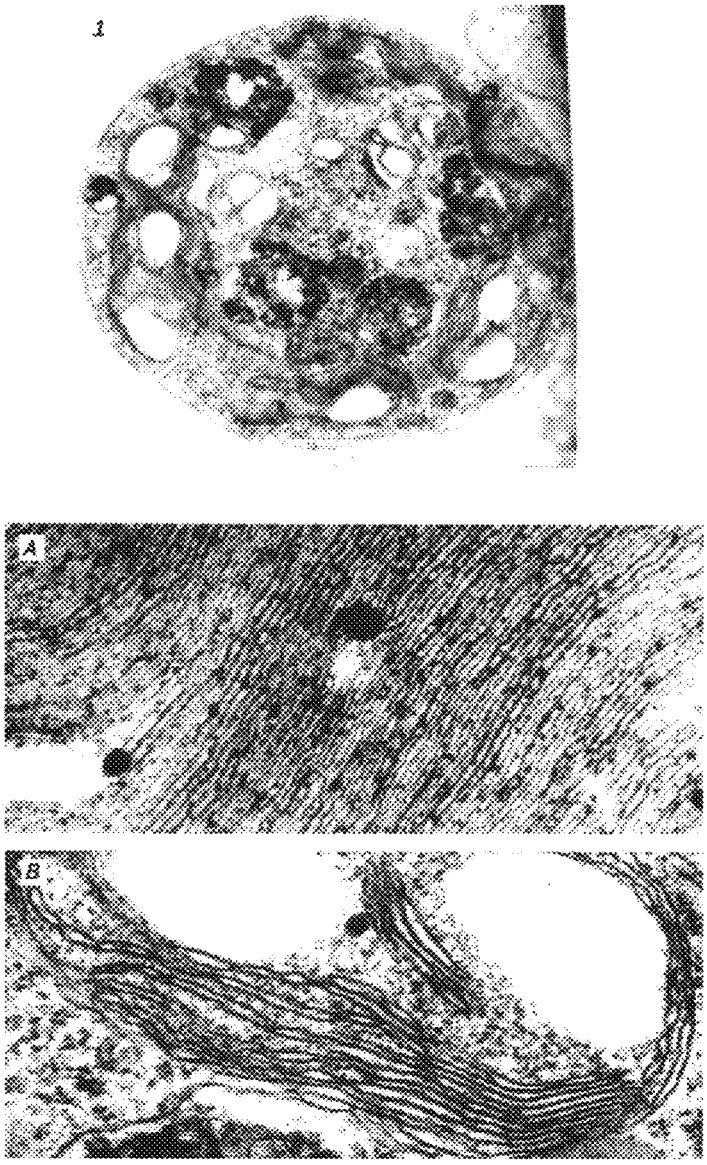

The novel variety 'DG8-108' was created by exposing wild-type *C. reinhardtii* 137-C to γ-radiation. 'DG8-108' cells may be range from 18-25 microns in length, are green in color (nearest color equivalent: Pantone #364; FIG. 1), and have either a spherical and/or ovate morphology. 'DG8-108' reproduces vegetatively by longitudinal fission of the cells. 'DG8-108' can be cultivated and maintained in agar (plates) or liquid culture. 'DG8-108' cultivated and maintained on agar plates with mineral medium form green colonies (nearest color equivalent: Pantone #364) that are 0.3-0.5 cm in diameter within 10 days. The size of individual 'DG8-108' cells is 60 to 80% greater than wild-type varieties. The size of 'DG8-108' colonies in 1.3-1.8 times greater than the size of wild-type colonies. Adult cells of 'DG8-108' have a very large chloroplast that occupies nearly ⅔ of the total cell volume, and the chloroplast has 1.9-2.0 (SD=0.4) times more thylakoid membranes compared to wild-type cells (FIG. 1-A, 1-B; Number of thylakoids calculated on basis of chloroplast cross section surface).

Figure 2:
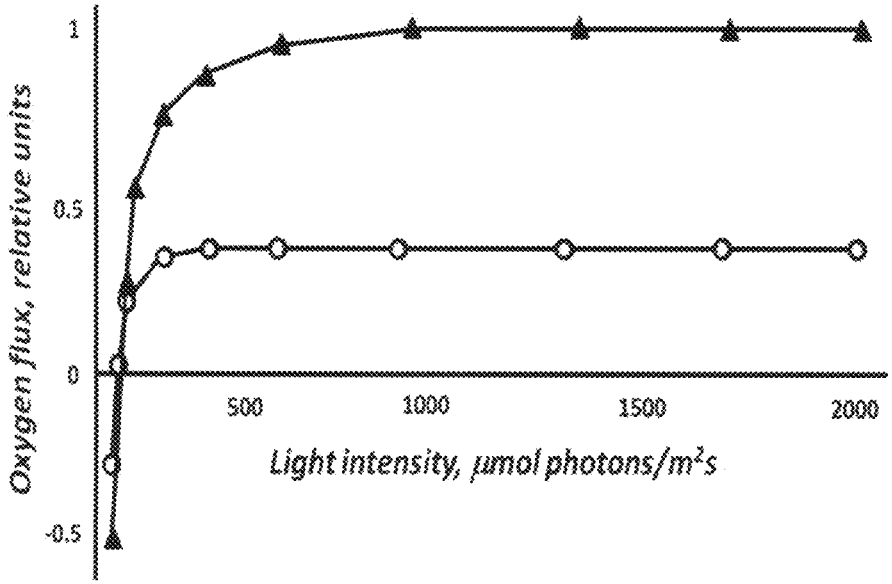

General physiological and specific plant physiological assays of photosynthetic productivity showed that 'DG8-108' possess physiological characteristics that distinguish it substantially from wild-type *C. reinhardtii* varieties. The total photosynthetic productivity of 'DG8-108', on both a gross and net basis is, at minimum, 2-2.5 times greater than wild-type (FIG. 2).

Figure 3:
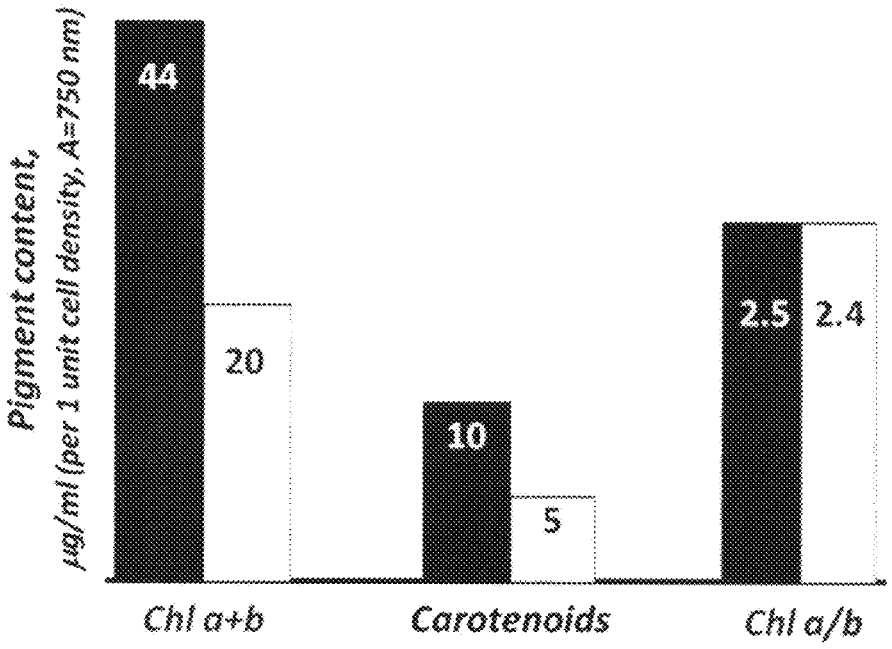
Figure 4:
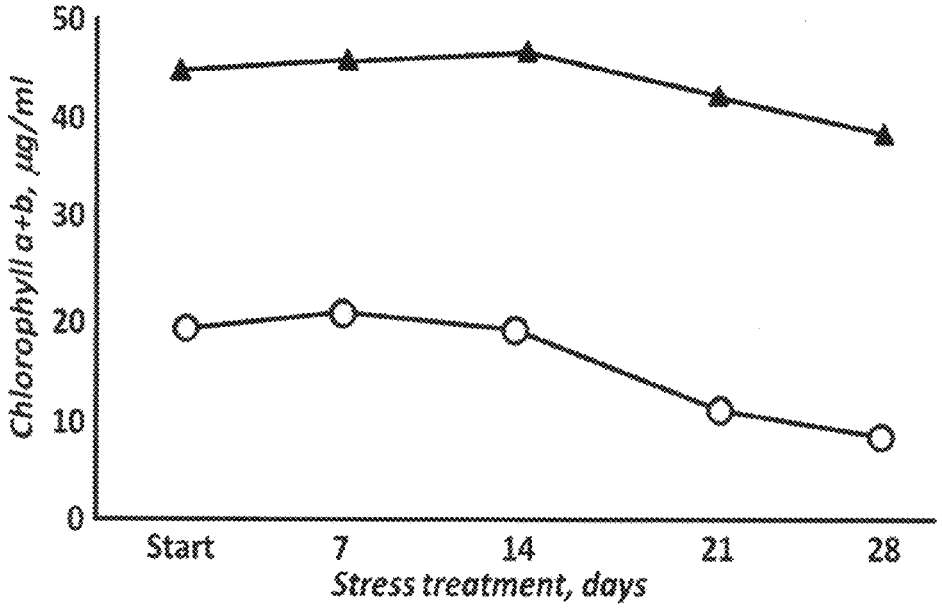

The chlorophyll content (chl a+chl b) of 'DG8-108' is nearly double that of the wild-type (FIG. 3) and persists even under chronic stress conditions (FIG. 4). The visual color difference between 'DG8-108' and 'wild-type' *C. reinhardtii* is due to the increased chlorophyll content of 'DG8-108' cells.

Figure 5:
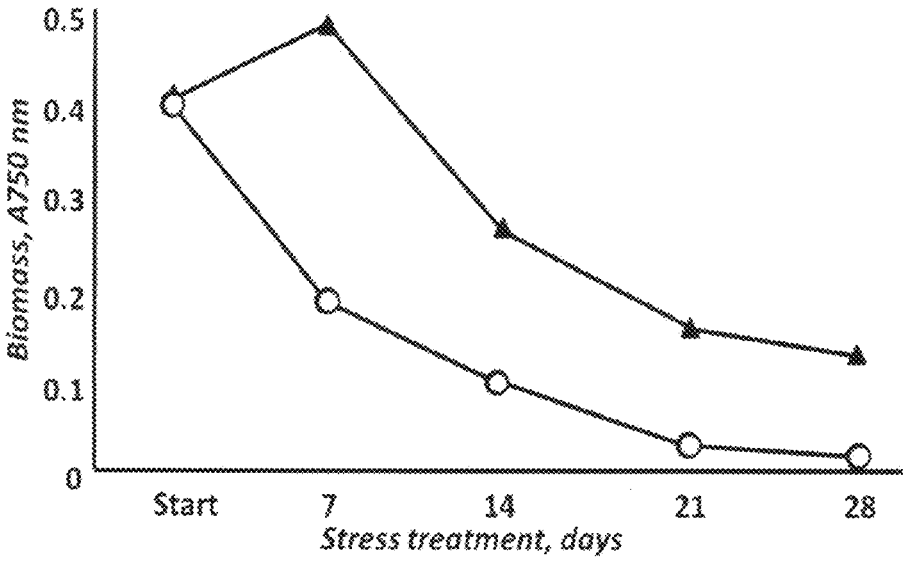

In addition, 'DG8-108' shows increased stress tolerance (higher pigment content and higher survivorship demonstrated (compared to wild-type varieties) to extreme environmental conditions (FIGS. 4 and 5).

II. SUMMARY OF THE INVENTION

A new and distinct variety of *Chlamydomonas reinhardtii* named 'DG8-108' was created by exposing wild-type *C. rein-*

*hardtii* 137-C to γ-radiation. The following traits distinguish *C. reinhardtii* variety 'DG8-108' from wild-type and other laboratory-created *C. reinhardtii* varieties known to the inventors:

1) Individual 'DG8-108' cells are larger in length and forms colonies on solid media that are up to 1.8 times larger than wild-type *C. reinhardtii.*
2) 'DG8-108' has higher photosynthetic rates—2.5 times higher—than wild-type *C. reinhardtii;*
3) 'DG8-108' has higher overall total productivity—2 times higher—compared to wild-type *C. reinhardtii;*
4) 'DG8-108' has the ability to accumulate 2 to 2.5 higher biomass levels compared to wild-type *C. reinhardtii;* and,
5) 'DG8-108' has the ability to maintain these enhanced physiological attributes under both optimal and stressful environmental conditions.

III. DESCRIPTION OF DRAWINGS

FIG. 1. Micrographs of *C. reinhardtii* variety 'DG8-108'. Ultrastructure of the whole cell (1; Differential Interference Contrast (DIC); 1,000× magnification) and close-ups of the chloroplast membranes in novel (Transmission Electron Microscopy; 65,000× magnification) 'DG8-108' (A) and wild-type (B) of 'DG8-108'.

FIG. 2. Productivity of wild-type *Chlamydomonas reinhardtii* and variety 'DG8-108'. Triangle—'DG8-108'; circle—wild-type.

FIG. 3. Pigment content in wild-type *Chlamydomonas reinhardtii* and variety 'DG8-108'. Dark—'DG8-108'; white—wild-type.

FIG. 4. Pigment content during stress treatment in wild-type *Chlamydomonas reinhardtii* and variety'DG8-108'. Triangle—'DG8-108'; circle—wild-type.

FIG. 5. Stress tolerance of wild-type *Chlamydomonas reinhardtii* and variety 'DG8-108' to complex stress conditions including: low light intensity (<42 μmol photons/$m^2$ s), low carbon dioxide level (<0.3%), low levels of nutritional compounds, and exposure to bacterial (*Escherichia coli*), coccus (*Staphylococcus* spp.) and fungal infection (*Penicillum* spp.), etc. Triangle—'DG8-108'; circle—wild-type.

IV. DETAILED METHODS, MORPHOLOGICAL AND PHYSIOLOGICAL DESCRIPTION

The novel variety 'DG8-108' was created by exposing wild-type *C. reinhardtii* 137-C to γ-radiation. The wild-type cells 137C(+) from agar (agar-Difco) plates were transferred into liquid mineral medium (without acetate) in a sterile box, and illuminated 10-12 hrs before finishing one cell division.

This suspension of young wild-type cells at a density 1 million cells per 1 ml of medium, was then treated with gamma-radiation at a dose 200 grays. Cobalt-60 was used as the γ-radiation source (60 grays from the top). At this dose, about 1% of the total cells survived. A suspension of surviving cells was then transferred into surface of agar-medium in Petri dishes. The density of grown cells should not be more than 200 colonies per Petri-dish. After 10-14 days growth, the surviving cells formed colonies of 3-5 mm in diameter. These colonies were separated, collected and, then analyzed for various morphological and physiological properties. The variety demonstrating the highest photosynthetic productivity among all the colonies analyzed was a dark green variety that was subsequently named: 'DG8-108'.

The novel *C. reinhardtii* variety named 'DG8-108' has the following characteristics that distinguish it from other wild-type and laboratory-isolated varieties of *C. reinhardtii:*

'DG8-108' cells may be range from 18-25 microns in length, whereas wild-type cells are 10-15 microns, and have either a spherical and/or ovate morphology.

'DG8-108' grown and maintained on agar (agar-Difco) plates with mineral medium (18-20 g/L agar), form dark green colonies that are 0.3-0.5 cm in diameter within 10 days. The size of 'DG8-108' colonies is 1.3-1.8 times greater than size of wild type colonies.

'DG8-108' grown and maintained in liquid media (made with either distilled or tap water because pH of medium is maintained using buffer) with 0.2% sodium acetate achieves cell densities of 40 million cells per milliliter within 48 hours. The mutant grown in mineral medium grows 1.5 times slower than in medium containing 0.2% acetate.

Solid and liquid mineral media contained the following compounds (mg/L): $NH_4CI$ (0.4); $MgSO_4 \cdot 7H_2O$ (0.1); $CaCl_2 \cdot 2H_2O$ (0.05); $K_2HPO_4$ (0.75); and $KH_2PO_4$ (0.36). In addition, a "microelement solution" was added to media at a concentration of 1 mg/L. This "microelement solution" contained the following compounds (mg/L): EDTA, sodium salt (50.00); $ZnSO_4 \cdot 7H_2O$ (22.00); $H_3BO_3$ (11.40); $MnCl_2 \cdot 4H_2O$ (5.06); $FeSO_4 \cdot 7H_2O$ (4.99); $CaCl_2 \cdot 6H_2O$ (1.61); $CuSO_4 \cdot 5H_2O$ (1.57); and $(NH_4)_6Mo_7O_{24} \cdot 4H_2O$ (1.10). To prevent precipitation, 0.5 grams per liter tri-sodium citric acid should be included in the microelement solution.

The optimal temperature for 'DG8-108' grown on agar medium is 23-25° C.; for mutants grown in liquid medium the optimal temperature is 27-35° C.

In natural conditions, 'DG8-108' may be cultivated in a very wide temperature range between 20° C. to 37° C.

The optimal light intensity for 'DG8-108' grown on agar is 42-56 μmol photons/$m^2$ s; for 'DG8-108' grown in liquid medium, the optimal light intensity is 182-210 μmol photons/$m^2$ s. The illumination for both conditions was delivered by mercury luminescence lamps (LB-40, white light).

The optimal pH of the growth medium is 6.8-7.2. Under culture using solid media (agar), the pH of the solid media may increase from 6.8 to 7.2 over a 14-day period under constant light conditions; in liquid medium, a similar pH change may occur in 4 days.

'DG8-108' grown in liquid medium achieves a total biomass of 5 to 10 grams fresh weight per liter after 3 days. The maximum total biomass achieved in 3 days is 20 grams fresh weight per liter.

'DG8-108' growth rate in solid or liquid culture is not affected by seasonal variation.

'DG8-108' growth rate may be increased by increasing the concentration of medium salts by 5 times compared to normal growth medium. Its doubling time can be decreased from 10-12 hours to 6 hours—and therefore, biomass levels will nearly double—due to increased salt levels.

V. LITERATURE CITED

Levine R P 1960 Genetic control of photosynthesis in *Chlamydomonas reinhardtii*. Proc. Nat. Acad. Sci. U.S.A., 16, 972.

What is claimed is:

1. A new and distinct variety of alga of the genus *Chlamydomonas*, named *Chlamydomonas reinhardtii* variety 'DG8-108', substantially as herein described and illustrated, which is principally characterized by having 2.5 times higher rates of photosynthesis, 2 times greater total productivity, 2 times greater biomass accumulation and higher environmental stress tolerance compared to wild-type.

* * * * *